United States Patent
Nabai

(10) Patent No.: US 10,231,495 B2
(45) Date of Patent: Mar. 19, 2019

(54) MEDICAL MASK WITH LOUPE LIGHT-COMPATIBLE EYE SHIELD

(71) Applicant: Sarah Nabai, Palo Alto, CA (US)

(72) Inventor: Sarah Nabai, Palo Alto, CA (US)

(*) Notice: Subject to any disclaimer, the term of this patent is extended or adjusted under 35 U.S.C. 154(b) by 287 days.

(21) Appl. No.: 14/062,801

(22) Filed: Oct. 24, 2013

(65) Prior Publication Data

US 2014/0109918 A1  Apr. 24, 2014

Related U.S. Application Data

(60) Provisional application No. 61/718,058, filed on Oct. 24, 2012.

(51) Int. Cl.
  *A61F 9/00* (2006.01)
  *A41D 13/11* (2006.01)
  *A61F 9/04* (2006.01)
  *A61B 90/30* (2016.01)
  *A61B 90/00* (2016.01)
  *A61B 90/50* (2016.01)

(52) U.S. Cl.
  CPC .......... *A41D 13/1184* (2013.01); *A61B 90/05* (2016.02); *A61B 90/30* (2016.02); *A61F 9/04* (2013.01); *A61B 2090/502* (2016.02)

(58) Field of Classification Search
  CPC .......................... A41D 13/1184; A41D 13/11; A41D 13/1107; A41D 13/1115; A41D 13/1123; A41D 13/1138; A41D 13/1161; A41D 13/1176; A41D 13/1192; A41D 13/05; A61B 19/72; A61B 19/5202; A61B 2019/262; A61B 90/05; A61B 90/30; A61B 2090/502; A61B 19/00; A61B 90/35; A61F 9/04; A61F 9/045; A61F 9/06; A61F 9/064; A61F 9/025; A61F 9/029; A61F 9/02; A61F 9/022; A62B 18/08; A62B 23/00; A62B 23/02; A62B 23/025; A62B 18/082; A62B 18/00; A62B 18/02; A62B 18/025
  USPC ............. 128/858, 857; 2/9, 209.13; 362/105
  See application file for complete search history.

(56) References Cited

U.S. PATENT DOCUMENTS

| | | | | |
|---|---|---|---|---|
| 2,765,789 A | * | 10/1956 | Schmierer | A61F 9/0008 604/308 |
| 2,881,443 A | * | 4/1959 | Barker, Jr. | A61F 9/025 2/9 |
| 2,762,050 A | | 9/1965 | Bricker | |
| 3,310,812 A | * | 3/1967 | Gaisser | A61F 9/02 2/174 |
| 3,328,806 A | * | 7/1967 | Allegro | A45D 44/12 2/174 |
| 4,323,063 A | | 4/1982 | Fisichella | |

(Continued)

*Primary Examiner* — Victoria J Hicks
(74) *Attorney, Agent, or Firm* — Shay Glenn LLP

(57) ABSTRACT

A face mask with full-face, wrap-around protection is disclosed. The face mask has a filter mask portion with an attached face shield portion and is adapted to be compatible with loupes and a loupe light. Specifically, the central portion of the face shield includes a horizontally centered cut out that extends downwardly from a top edge. The cut out is sized and positioned to allow a loupe light to pass through. The central portion of the face shield is hingedly connected to a pair of side portions. The side portions may include openings that allow straps from the filter mask to pass through and secure the side portions against the head.

18 Claims, 4 Drawing Sheets

(56) References Cited

U.S. PATENT DOCUMENTS

| | | |
|---|---|---|
| 4,837,862 A * | 6/1989 | Heil ................ A61F 9/045 |
| | | 2/12 |
| 4,856,509 A | 8/1989 | Lemelson |
| 4,920,960 A | 5/1990 | Hubbard et al. |
| 4,944,294 A | 7/1990 | Borek, Jr. |
| 5,020,533 A | 6/1991 | Hubbard et al. |
| 5,150,703 A | 9/1992 | Hubbard et al. |
| D355,715 S | 2/1995 | Hubbard et al. |
| 5,682,879 A | 11/1997 | Bowers |
| 5,813,398 A * | 9/1998 | Baird ................ A41D 13/1115 |
| | | 128/201.15 |
| 6,026,511 A * | 2/2000 | Baumann ........... A41D 13/1184 |
| | | 128/201.17 |
| D440,652 S | 4/2001 | Pollard |
| 6,213,125 B1 * | 4/2001 | Reese ................ A41D 13/1115 |
| | | 128/857 |
| 6,698,427 B1 | 3/2004 | Clowers |
| D530,418 S | 10/2006 | Henry et al. |
| 7,191,778 B2 | 3/2007 | Shue et al. |
| 7,681,256 B2 | 3/2010 | Fullerton et al. |
| 7,823,224 B2 | 11/2010 | Fullerton et al. |
| 7,992,558 B2 | 8/2011 | Thornton et al. |
| 8,020,276 B2 | 9/2011 | Thornton |
| 8,051,855 B2 | 11/2011 | Ho et al. |
| 2011/0179540 A1 | 7/2011 | Sutton |
| 2011/0203594 A1 | 8/2011 | Brain |
| 2011/0239347 A1 | 10/2011 | Beliveau |
| 2016/0353815 A1 | 12/2016 | Nabai |

\* cited by examiner

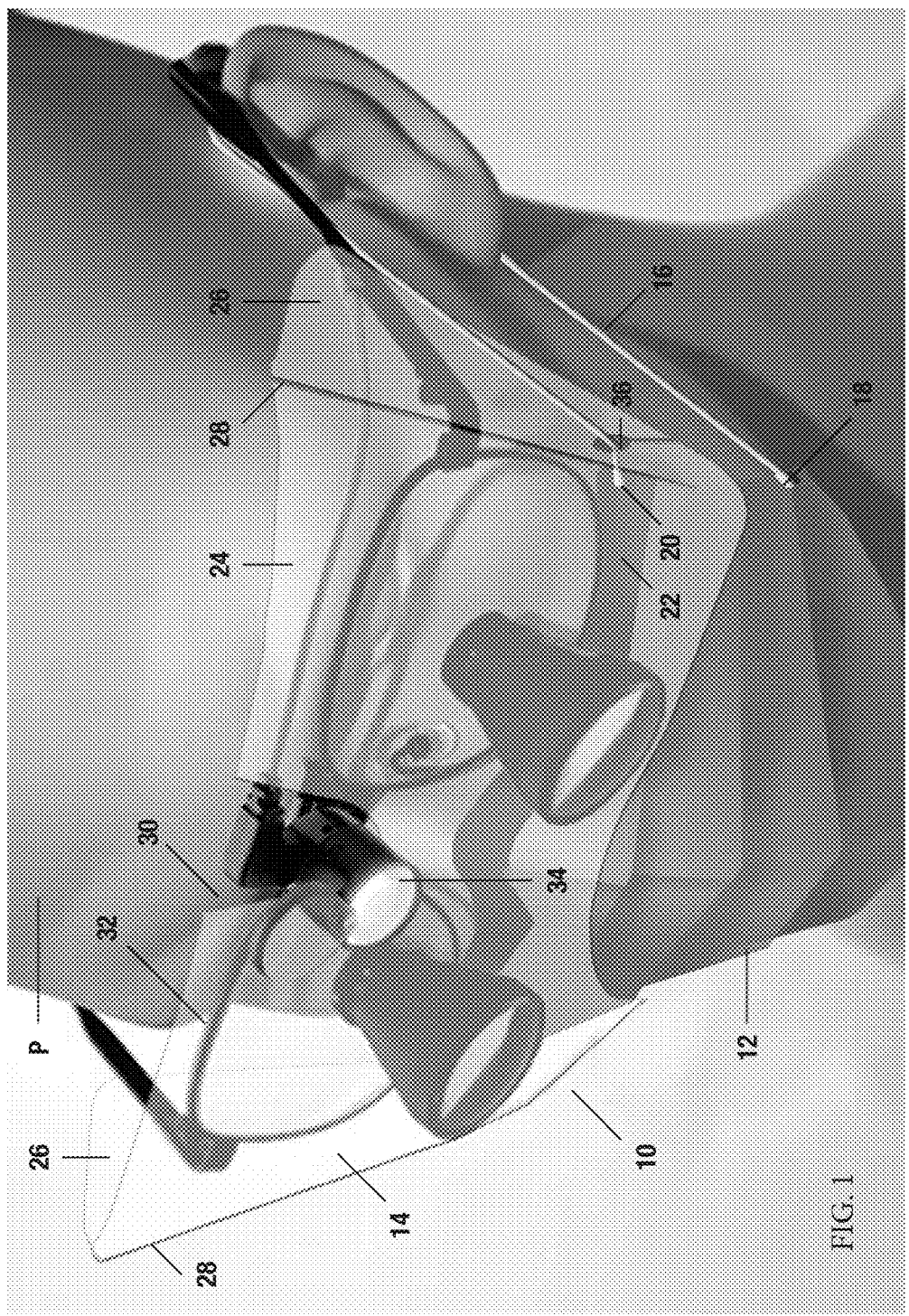

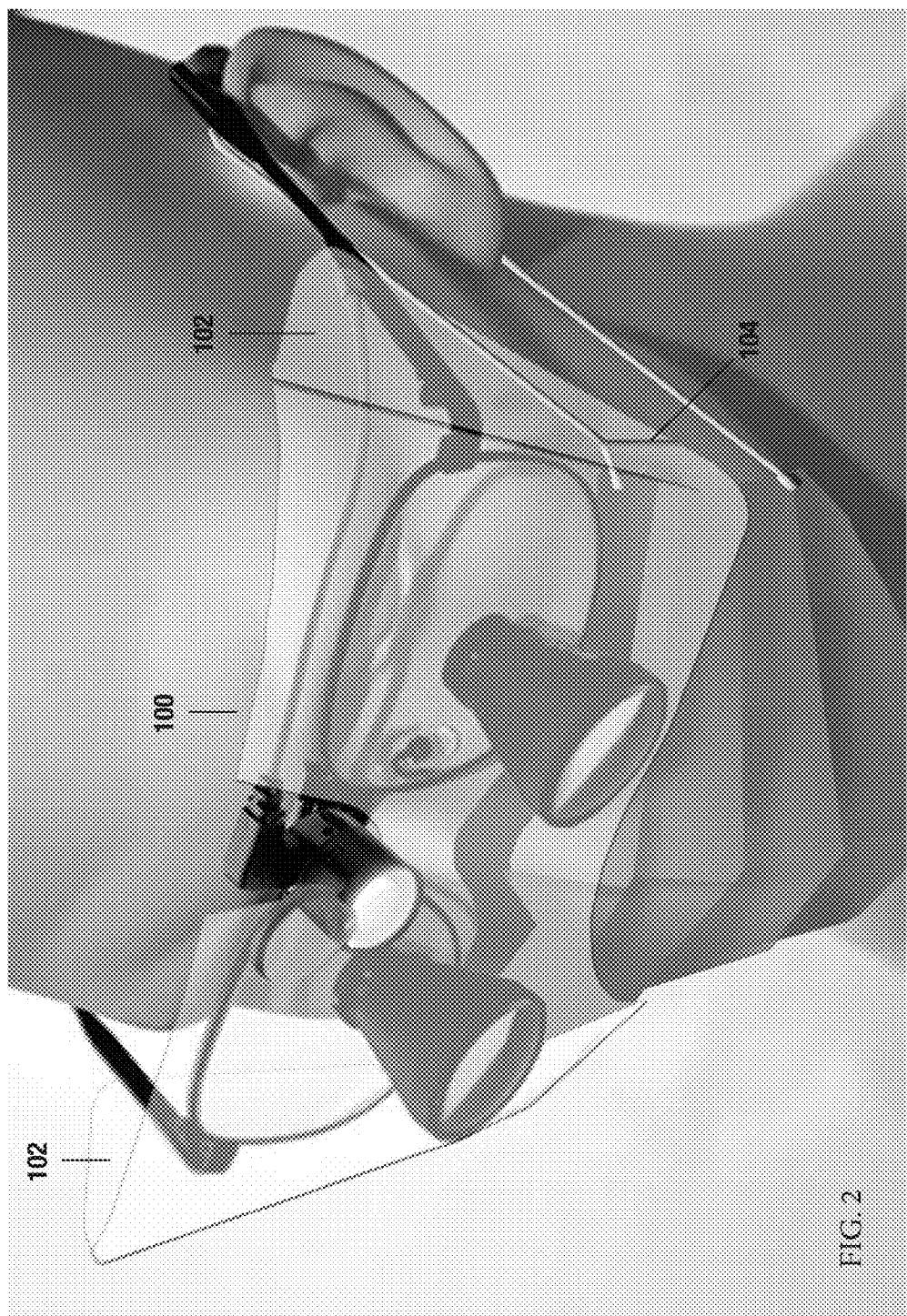

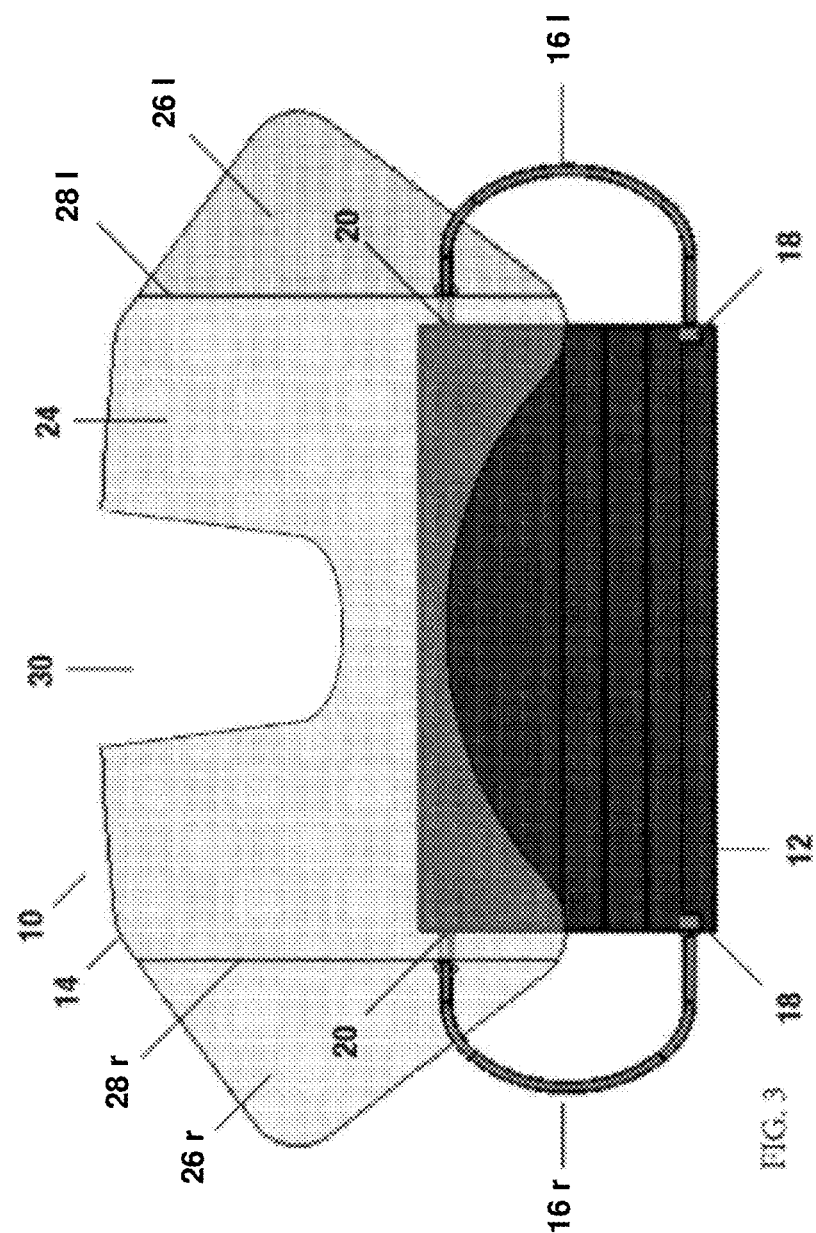

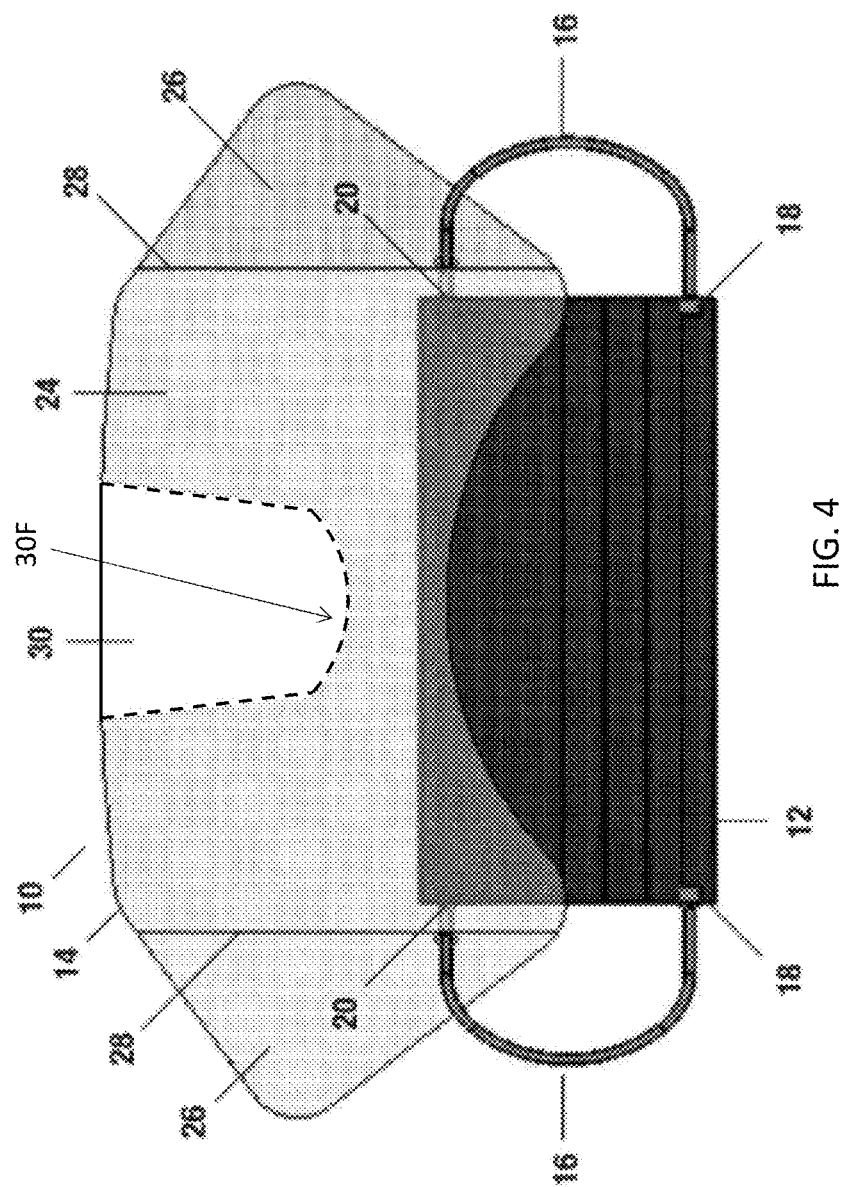

MEDICAL MASK WITH LOUPE LIGHT-COMPATIBLE EYE SHIELD

CROSS-REFERENCE TO RELATED APPLICATIONS

This application claims priority to U.S. Provisional Patent Application No. 61/718,058, filed Oct. 24, 2013. That application is incorporated by reference in its entirety.

BACKGROUND OF THE INVENTION

1. Field of the Invention

The invention relates to disposable body substance isolation equipment, and in particular, to medical masks with eye shields that are compatible with loupe lights.

2. Description of Related Art

Over the last several decades, both medical professionals and the general public have become far more aware of the dangers of pathogens in bodily fluids. Some of the pathogens themselves have become increasingly virulent, and drug resistance has become an issue with strains of bacteria that were once easily eradicated using standard antibiotics.

Products that are intended to prevent a medical practitioner from coming into contact with potentially infectious bodily fluids are referred to generally as body substance isolation (BSI) equipment. One of the most common types of BSI is the face mask.

Face masks exist in several forms, perhaps the most common of which is the filter mask. A filter mask is essentially a piece of material that is worn over the nose and mouth to filter the incoming and outgoing breath, thus preventing the wearer from being infected by others and others from being infected by the wearer. The filter mask is typically tied around the back of the head and neck, or includes elastic straps that are looped over the ears. Surgeons typically wear this kind of face mask during most surgical procedures, and some patients with chronic conditions, like tuberculosis, may routinely wear filter masks to prevent others from becoming infected.

Filter masks may be adequate for some applications where small droplets in the breath are the primary concern. However, for applications in which blood and other bodily fluids may splash or splatter, full-face protection may be more desirable. For example, full-face protection is becoming increasingly common in dental offices, where the dentist or hygenist has close contact with the patient.

There are several common options for full-face protection. The first, and perhaps most complete, is a helmet-style shield that fits over the head and covers the face entirely. In some versions, the face shield portion may rotate up and out of the way when not needed. Although effective and able to offer full wrap-around protection of the head and face, this equipment is cumbersome, and can be hot and uncomfortable to wear.

A second, lighter option is a filter mask with an integrated plastic face shield. In masks of this sort, a clear piece of plastic is attached to and around the filter mask and extends upwardly to cover the face. While useful, and often more comfortable than a helmet-style shield, these disposable integrated face shields often do not have good wrap-around coverage of the face, i.e., they may offer poor protection for the side of the face and are not contoured to fit the face well.

Another problem with the standard disposable integrated face shield is that medical providers often wear glasses or other equipment on their faces. For example, it is extremely common for a medical provider to wear a set of loupes. Loupes bear a general resemblance to glasses, and typically include magnifiers (2.5× and 3.5× are common magnifications) as well as a light. When worn, a loupe light is typically centered on the brow, just above the bridge of the nose. Unfortunately, standard disposable face shields cannot accommodate this kind of equipment, which projects out from the face.

SUMMARY OF THE INVENTION

One aspect of the invention relates to a face mask. The face mask has a filter mask portion with an attached face shield portion and is adapted to be compatible with loupes and a loupe light. Specifically, the central portion of the face shield includes a horizontally centered cut out that extends downwardly from a top edge. The cut out is sized and positioned to allow a loupe light to pass through. The central portion of the face shield is hingedly connected to a pair of side portions. The side portions may include openings that allow straps from the filter mask to pass through and secure the side portions against the head. In some embodiments, the central portion may include a frangible section that can be removed to create the cut out.

These and other aspects, features, and advantages of the invention will be described below.

BRIEF DESCRIPTION OF THE DRAWING FIGURES

The invention will be described with respect to the following drawing figures, in which like numerals represent like features throughout the drawings, and in which:

FIG. 1 is a perspective view of a medical mask with a loupe light-compatible eye shield according to one embodiment of the invention;

FIG. 2 is a perspective view of a medical mask according to another embodiment of the invention; and FIG. 3 is a front elevational view of the mask of FIG. 1.

FIG. 4 is a front elevation view of the mask of FIGS. 1 and 3 showing a perforated and frangible portion that may be removed to form a cut out.

DETAILED DESCRIPTION

FIG. 1 is a perspective view of a medical mask with a loupe light-compatible eye shield, generally indicated at 10, according to one embodiment of the invention, shown as worn on the head of a person P. The medical mask 10 includes both a filter mask portion 12 and a face shield portion 14.

The filter mask portion 12 is a pleated sheet of natural or polymer fibers that is extended over the nose and the mouth, down to and beyond the level of the chin. The construction of filter masks is well known in the art, and any known materials may be used for the filter mask portion 12. The material of which the filter mask portion 12 is made may depend on any number of factors, including the size of particulate or aerosol matter that the filter mask portion 12 is intended to filter. In the illustrated embodiment, the medical mask 10 and filter mask portion 12 are secured by a pair of elastic straps 16, each of which is secured to the filter mask portion 12 at two locations 18, 20. As best seen in FIG. 3, a left side strap 16r is attached to the left side of the filter mask portion and a right side strap 16r is attached to the right side of the filter mask portion. Depending on the embodiment, the straps 16 may be sewn or fused to the filter mask portion 12, or simply passed through it and knotted. Of course, inextensible tied straps or other methods of securement may be used instead of elastic straps 16.

Provided above the filter mask portion 12 and covering the eyes, brow, and sides of the face in FIG. 1 is the face shield portion 14. The face shield portion 14 is attached at its left and right edges to the left and right edges of the filter mask portion 12, typically by fusing, adhesives, or any other known means. The bottom edge of the face shield portion 14 is typically free to move relative to the filter mask portion portion 12, and an upper strip 22 of the filter mask portion 12 includes an embedded malleable metal strip that can be contoured to fit the nose. As shown, there is some overlap between the filter mask portion 12 and the face shield portion 14; the face shield portion 14 extends below the top of the filter mask portion 12 and terminates in a concave curve with a high point proximate to the tip of the nose, which helps to accommodate the nose. Of course, the bottom curvature of the filter mask portion 12 may vary from embodiment to embodiment, and in some embodiments, the filter mask portion 12 may be squared off.

The face shield portion 14 itself is made from a thin, transparent sheet of material, and includes a central section 24 and two side portions 26. As shown in the various views of the drawings, the two side portions 26 are on the left side and the right side of the central section 24. The left side portion is designated 26*l* and the right side portion is designated 26*r*. The side portions 26 are connected to the central section 24 by respective hinges 28, which may, for example, be living hinges or scores that allow the two side portions 26 to fold and bend relative to the central section 24. A left side hinge 28*l* connects the left side portion 26*l* and the central section 24. A right side hinge 28*r* connects the right side portion 26*r* and the central section 24. This, in turn, may allow better coverage of the sides of the face as compared with conventional face masks, in which there are no hinges and the plastic simply wraps around the face as best it can. The hinges 28 may also reduce the tendency for the face shield portion 14 to warp, crimp, or distort, which may interfere with the provider's view or be uncomfortable.

Additionally, the central section 24 of the face shield portion 14 defines a cut out 30. The cut out 30 is essentially horizontally centered on the face shield portion 14, and extends downwardly from a top edge of the face shield portion 14. As shown in FIG. 1, when a user is wearing loupes 32 with a loupe light 34, the cut out 30 allows the loupe light 34 to pass through the face shield portion 14, thus making it easier to wear loupes 32, a loupe light 34, and the mask 10 at the same time.

The cut out 30 of the illustrated embodiment is wider at the top and narrower at the bottom, and the bottom may be rounded (i.e., to match or approximate the curvature of a typical loupe light 34). The shape of the cut out 30 may be different in other embodiments—for example, the bottom may be squared, and the top may have a different taper or no taper at all. In one embodiment, for example, the cut out 30 may be about 2.5 inches at its top, about 2 inches at its bottom, and with a height of about 2.5 inches, which provides enough room to accommodate a typical loupe light 34. However, other embodiments may use different dimensions, and as was noted above, the cut out 30 need not taper in all embodiments.

In some embodiments, masks 10 may be made with no cut out 30. In other embodiments, masks may be made with a perforated frangible portion that can be torn off to create a cut out like the cut out 30 illustrated in FIG. 1. FIG. 4 illustrates an embodiment of a mask 10 having a perforated frangible portion 30*f* sized and shaped to create a cut out 30.

Of course, the user is under no obligation to remove a frangible portion if one is present, and may use a face mask without removing a frangible portion if, for example, he or she does not wish to wear a loupe light.

In embodiments of the invention, the straps 16 or ties that secure the mask 10 to its wearer may cooperate with the side portions 26 to secure them around the sides of the face or otherwise maintain their position, creating a wrap-around effect.

As shown in FIG. 1, the top half of each elastic strap 16 passes through a hole 36 defined toward the bottom of the side portion 26, emerges on the outside of the side portion 26 and, because of the tension in it, presses against the side portion 26 and keeps it against the face as the strap 16 extends toward and around the ear.

Each hole 36 may be reinforced, for example, by an additional layer or layers of plastic fused or sintered around each hole 36. However, the holes 36 need not be reinforced. In fact, the side portion 26 need not have a hole 36 per se; instead, any kind of opening of sufficient size to allow the strap 16 to pass may be used. As one example, FIG. 2 is a perspective view similar to the view of FIG. 1 illustrating another embodiment of the invention, generally indicated at 100. The face mask 100 has essentially the same features as the mask 10 described above. However, in each side portion 102, a slit 104 extends from the bottom edge up. The slit 104 has an upwardmost point at about the same position where a hole 36 would be in mask 10. In some embodiments, the slit 104 may terminate in a hole, although it need not. In some embodiments, there may be no opening in the side portion 26, 102 at all.

FIG. 3 is a front elevational view of the mask 10 of FIG. 1, illustrating how the mask 10 appears when not in use. One advantage of the mask 10 is that when not in use, it is essentially flat, making it easier to package and ship. However, it should be understood that although the filter mask portion 12 of the illustrated embodiment is a pleated flexible material that contours to the face, in other embodiments, the filter mask portion could be a dome-shaped mask with sufficient rigidity to hold its own shape. Masks of this type are known, and are often used to filter dust and other particulate matter.

While the invention has been described with respect to certain embodiments, the description is intended to be exemplary, rather than limiting. Modifications and changes may be made within the scope of the invention, which is defined by the appended claims.

What is claimed is:

1. A face mask for use by a wearer wearing a set of loupes having a pair of magnifiers and a light between the pair of magnifiers, comprising:
    a filter mask portion including a filter material adapted to be disposed over the nose and mouth of the wearer and a pair of straps, a left strap of the pair of straps adapted to secure the filter mask portion about a left ear of the wearer and a right strap of the pair of straps adapted to secure the filter mask portion about a right ear of the wearer;
    a face shield portion made of a transparent, flexible material, the face shield portion being connected to the filter mask portion and extending upwardly therefrom in a position to protect an outer face of each of the magnifiers in the pair of magnifiers and
    having a central section that defines a cut out on the face shield portion and extending from a top edge thereof downwardly, the cut out sized and positioned to permit the light to pass through the cut out and extend beyond the central section; and
a left side hinge connecting a left side portion to the central section;
a right side hinge connecting a right side portion to the central section;
wherein a lower most aspect of the face shield portion extends beyond and overlaps an upper most edge of the filter mask portion and the lower most aspect of the face shield portion having curved lower edge extending between the left side hinge portion and the right side hinge portion with a high point proximate to the cut out,
wherein the cut out is widest along the top edge of the face shield portion and narrows as the cut out extends downwardly towards where the lowermost aspect of the face shield portion overlaps the upper most edge of the filter mask portion.

2. The face mask of claim 1, wherein the left side portion includes a left side opening adjacent to the left side hinge and the left strap of the pair of straps passes through the left side opening such that the left strap of the pair of straps abuts an exterior surface of the left side portion and the right side portion includes a right side opening adjacent to the right side hinge and the right strap of the pair of straps passes through the right side opening such that the right strap of the pair of straps abuts an exterior surface of the right side portion.

3. The face mask of claim 2, wherein the left side opening adjacent to the left side hinge comprises a slit and the right side opening adjacent to the right side hinge comprises a slit.

4. The face mask of claim 3, wherein the slit in the right side portion extends upwardly from a lower edge of the right side portion and the slit in the left side portion extends upwardly from a lower edge of the left side portion.

5. The face mask of claim 1, wherein the left strap or right strap further comprises: a pair of straps, vertically spaced from one another.

6. The face mask of claim 5, wherein the pair of straps are elastic.

7. The face mask of claim 1, wherein a bottom edge of the cut out closest to the lowermost aspect of the face shield portion is rounded.

8. The face mask of claim 1, wherein the central section of the face shield portion further comprises a frangible portion adapted to be broken away from the central section to define the cut out.

9. The face mask of claim 1, wherein left and right side edges of the face shield portion are connected to respective left and right side edges of the filter mask portion.

10. The face mask of claim 1, wherein the lower most aspect of the face shield portion extends below a top portion of the filter mask portion.

11. The face mask of claim 1, the cut out further comprising sidewalls wherein the sidewalls taper towards a rounded bottom portion.

12. A face mask for use by a wearer wearing a set of loupes having a pair of magnifiers and a light between the pair of magnifiers, comprising:
a filter mask portion including a filter material adapted to be disposed over the nose and mouth of the wearer and a pair of straps, a left strap of the pair of straps adapted to secure the filter mask portion about a left ear of the wearer and a right strap of the pair of straps adapted to secure the filter mask portion about a right ear of the wearer;
a face shield portion made of a transparent, flexible material, the face shield portion being connected to the filter mask portion and extending upwardly therefrom in a position to protect an outer face of each of the magnifiers in the pair of magnifiers and
having a central section that comprises a frangible portion adapted to be broken away from the central section to define a cut out on the face shield portion and extending from a top edge thereof downwardly, the cut out sized and positioned to permit the light to pass through the cut out and extend beyond the central section;
a left side hinge connecting a left side portion to the central section;
a right side hinge connecting a right side portion to the central section; and
wherein a lower most aspect of the face shield portion extends beyond and overlaps an upper most edge of the filter mask portion and the lower most aspect of the face shield portion having curved lower edge extending between the left side hinge and the right side hinge with a high point proximate to the cut out.

13. The face mask of claim 12, wherein the left side portion includes a left side opening adjacent to the left side hinge and the left strap of the pair of straps passes through the left side opening such that the left strap of the pair of straps abuts an exterior surface of the left side portion and the right side portion includes a right side opening adjacent to the right side hinge and the right strap of the pair of straps passes through the right side opening such that the right strap of the pair of straps abuts an exterior surface of the right side portion.

14. The face mask of claim 13, wherein the left side opening adjacent to the left side hinge comprises a slit and the right side opening adjacent to the right side hinge comprises a slit.

15. The face mask of claim 14, wherein the slit in the right side portion extends upwardly from a lower edge of the right side portion and the slit in the left side portion extends upwardly from a lower edge of the left side portion.

16. The face mask of claim 12, wherein the cut out is widest along the top edge of the face shield portion and narrows as the cut out extends downwardly towards where the lowermost aspect of the face shield portion overlaps the upper most edge of the filter mask portion.

17. The face mask of claim 12, wherein a bottom edge of the cut out closest to the lowermost aspect of the face shield portion is rounded.

18. A face mask for use by a user wearing a pair of loupes, comprising:
a filter mask portion including a filter material adapted to be disposed over the nose and mouth of the user;
a face shield portion made of a transparent, flexible material, the face shield portion being connected to the filter mask portion and extending upwardly therefrom and having
a central section that includes a frangible portion defining a cut out essentially horizontally centered on the face shield portion and extending from a top edge thereof downwardly, the cut out having side walls and a bottom portion sized and positioned to permit a loupe light coupled to the pair of loupes to pass through the cut out when the frangible portion is separated from the central section, and
a face shield left side portion hingedly attached to the central section and adapted to fold when the face mask is worn by the user, a face shield right side portion hingedly attached to the central section and adapted to fold when the face mask is worn by the user;

an elastic strap attached to a left side of the filter mask portion passes through a slit in the face shield left side portion and over an exterior surface of the face shield left side portion before terminating on the left side of the filter mask portion;

an elastic strap attached to a right side of the filter mask portion passes through a slit in the face shield right side portion and over an exterior surface of the face shield right side portion before terminating on the right side of the filter mask portion;

wherein the face shield portion overlaps the filter mask portion and terminates in a concave lower edge with a high point proximate a central upper position of the filter mask portion.

\* \* \* \* \*